(12) United States Patent
Curnow et al.

(10) Patent No.: US 7,780,136 B2
(45) Date of Patent: Aug. 24, 2010

(54) SURGICAL TRAY CORNER PROTECTOR

(75) Inventors: Sam Curnow, Chanhassen, MN (US); Ted Eric Ahrenholtz, Plymouth, MN (US)

(73) Assignee: General Hospital Supply Corporation, Monroe, NC (US)

( * ) Notice: Subject to any disclaimer, the term of this patent is extended or adjusted under 35 U.S.C. 154(b) by 0 days.

(21) Appl. No.: 12/206,437

(22) Filed: Sep. 8, 2008

(65) Prior Publication Data

US 2009/0000982 A1    Jan. 1, 2009

Related U.S. Application Data

(63) Continuation of application No. 11/950,246, filed on Dec. 4, 2007, now Pat. No. 7,422,185, which is a continuation of application No. 11/779,089, filed on Jul. 17, 2007, now Pat. No. 7,413,157, which is a continuation of application No. PCT/US2006/030297, filed on Aug. 2, 2006.

(60) Provisional application No. 60/705,245, filed on Aug. 3, 2005.

(51) Int. Cl.
*A47B 95/00* (2006.01)

(52) U.S. Cl. .................. 248/345.1; 248/346.5; 206/453; 206/586

(58) Field of Classification Search .................. 248/673, 248/678, 345.1, 346.01, 346.02, 94, 346.11, 248/346.4, 346.5; 206/77.1, 453, 586; 428/99, 428/119, 35.7, 36.5, 36.8, 36.92
See application file for complete search history.

(56) References Cited

U.S. PATENT DOCUMENTS

| | | | |
|---|---|---|---|
| 259,425 | A | 12/1882 | Jennison |
| 450,349 | A | 4/1891 | Arnold |
| 539,698 | A | 5/1895 | Milligan |
| 601,831 | A | 4/1898 | Hayden, Jr. |
| 797,495 | A | 8/1905 | Clark |
| D154,903 | S | 8/1949 | Caldwell |
| 4,852,744 | A | 8/1989 | Van Breemen |
| 4,993,546 | A | 2/1991 | Southard |
| 5,165,539 | A | 11/1992 | Weber et al. |
| 5,424,048 | A | 6/1995 | Riley |
| 5,549,868 | A | 8/1996 | Carlson, II |
| 5,680,929 | A | 10/1997 | Von Seidel |
| 5,766,561 | A | 6/1998 | Frieze et al. |
| 5,992,812 | A | 11/1999 | Mark |
| 6,003,169 | A | 12/1999 | Davis, Jr. |
| 6,036,155 | A | 3/2000 | Tsui |
| 6,257,540 | B1 | 7/2001 | Kresch |
| 6,776,380 | B1 | 8/2004 | Kirk, Jr. et al. |
| 2003/0038054 | A1 | 2/2003 | Hurley et al. |
| 2005/0244316 | A1 | 11/2005 | Davis |
| 2006/0243636 | A1 | 11/2006 | Robichaud et al. |

*Primary Examiner*—J. Allen Shriver, II
*Assistant Examiner*—Bradley H Duckworth
(74) *Attorney, Agent, or Firm*—Kinney & Lange, P.A.

(57) ABSTRACT

A surgical tray corner protector includes a support base, a side wall extending along an edge of the support base, and a plurality of apertures extending through the support base to form a tray support surface, providing improved drainage and air flow.

6 Claims, 5 Drawing Sheets

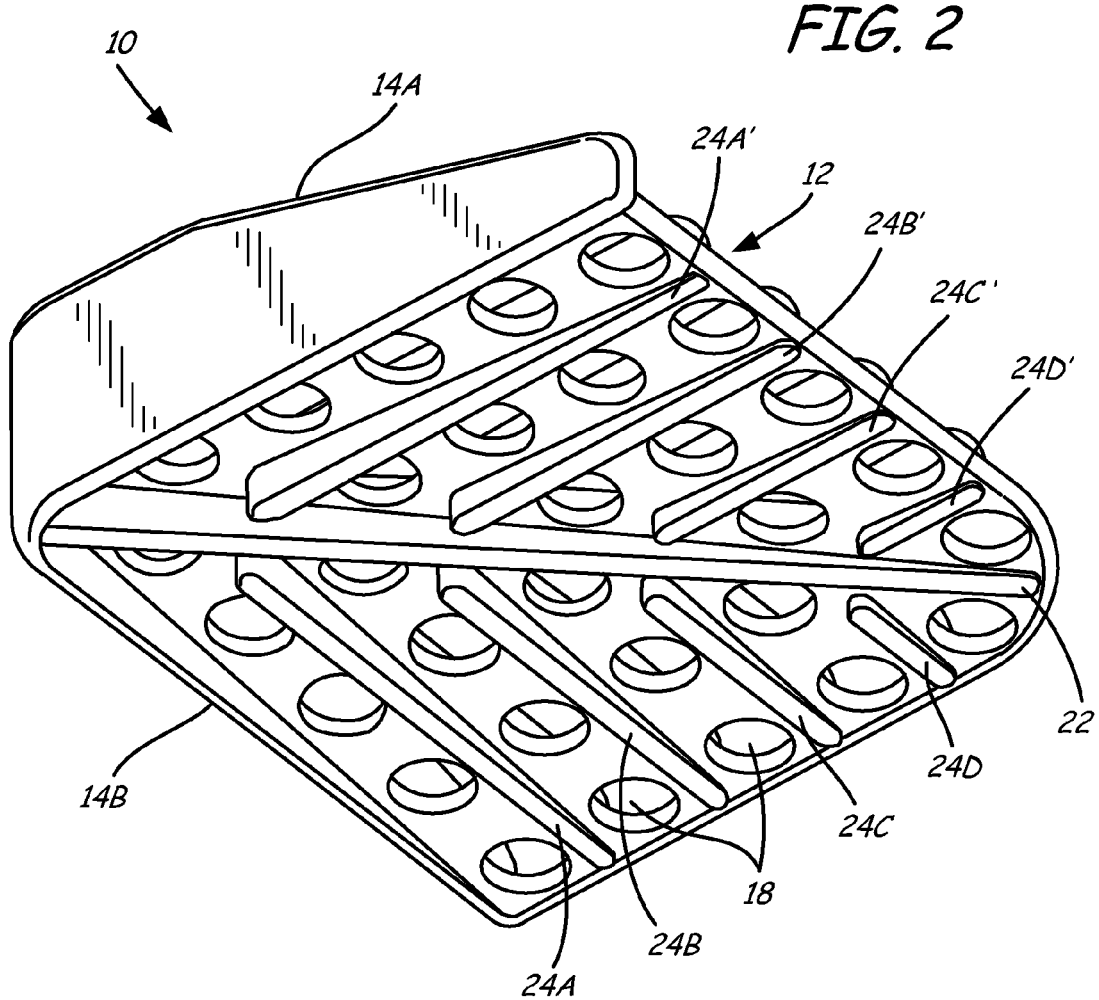

SURGICAL TRAY CORNER PROTECTOR

CROSS-REFERENCE TO RELATED APPLICATION(S)

This application is a continuation of U.S. application Ser. No. 11/950,246 entitled "Surgical Tray Corner Protector" filed Dec. 4, 2007 by S. Curnow and T. Ahrenholtz, which is a continuation of U.S. application Ser. No. 11/779,089 entitled "Surgical Tray Corner Protector" filed Jul. 17, 2007 by S. Curnow and T. Ahrenholtz, which is a continuation of PCT Application No. PCT/US2006/030297 filed Aug. 2, 2006, which claims the benefit of U.S. Provisional Application No. 60/705,245 filed Aug. 3, 2005.

INCORPORATION BY REFERENCE

The aforementioned U.S. application Ser. No. 11/950,246, U.S. application Ser. No. 11/779,089, PCT Application No. PCT/US2006/030297 and U.S. Provisional Application No. 60/705,245 are hereby incorporated by reference in their entirety.

BACKGROUND

This invention relates to a corner protector for a surgical tray. More specifically, this invention relates to a surgical tray corner protector comprising a base, a side wall which extends from an outer edge of the base, and support members extending from the base to form a tray support surface, providing improved drainage and air flow.

In hospitals, surgery centers, and other healthcare facilities, surgical instruments must be sterilized prior to use. Normally, surgical instruments are placed in a surgical tray, which is wrapped in a sterilization wrap to protect the instruments from subsequent contamination. The wrapped surgical tray is then inserted into an autoclave and sterilized.

After sterilization, the wrapped tray is placed on a storage shelf or cart until it is needed for a surgical procedure. When the surgical instrument sterilization tray is needed, it is delivered to the operating room. Before the surgical tray is unwrapped, the integrity of the sterilization wrap is inspected to ensure that it does not contain any rips, tears or holes. If the wrap is compromised, the instruments are considered contaminated and can not be used.

Most sterilization wrap is susceptible to tearing and ripping. Handling by hospital staff is the primary cause of ripping of sterilization wrap on a surgical tray. Many of the surgical trays used in healthcare facilities are heavy and/or have sharp corners. When the wrapped surgical tray is slid across a surface, instead of being directly lifted, the corners of the surgical tray can puncture the wrap, thus destroying the sterile environment in which the surgical instruments are stored.

If the sterilization wrap on a surgical tray is torn, the surgical instruments must be rewrapped and sterilized again, which results in reprocessing costs and takes up staff time. In addition, surgical procedures may consequently be delayed. Thus, there is a need in the art for a surgical tray corner protector that will prevent sterilization wrap surrounding a sterile surgical tray from being ripped or torn by the corners of the tray, and, therefore, rendering the surgical instruments unsterile.

SUMMARY

The present invention prevents the sterilization wrap surrounding a sterile surgical tray from being compromised by rips and tears during transportation and storage. The present invention is a corner protector configured to be positioned against a corner of a surgical tray. The corner protector comprises a support base, a side wall extending along an edge of the support base and having an inner surface and an outer surface, and a plurality of apertures extending through the support base. The support base and side wall are composed of a medical grade polymeric material and are configured to receive a corner of the surgical tray such that the support base contacts a bottom panel of the surgical tray and the inner surface of the side wall is positioned adjacent to a side panel of the surgical tray to form a protective barrier around the corner of the surgical tray.

BRIEF DESCRIPTION OF THE DRAWINGS

FIG. 2 is a bottom perspective view of the surgical tray corner protector of FIG. 1.

DETAILED DESCRIPTION

Figure 1:
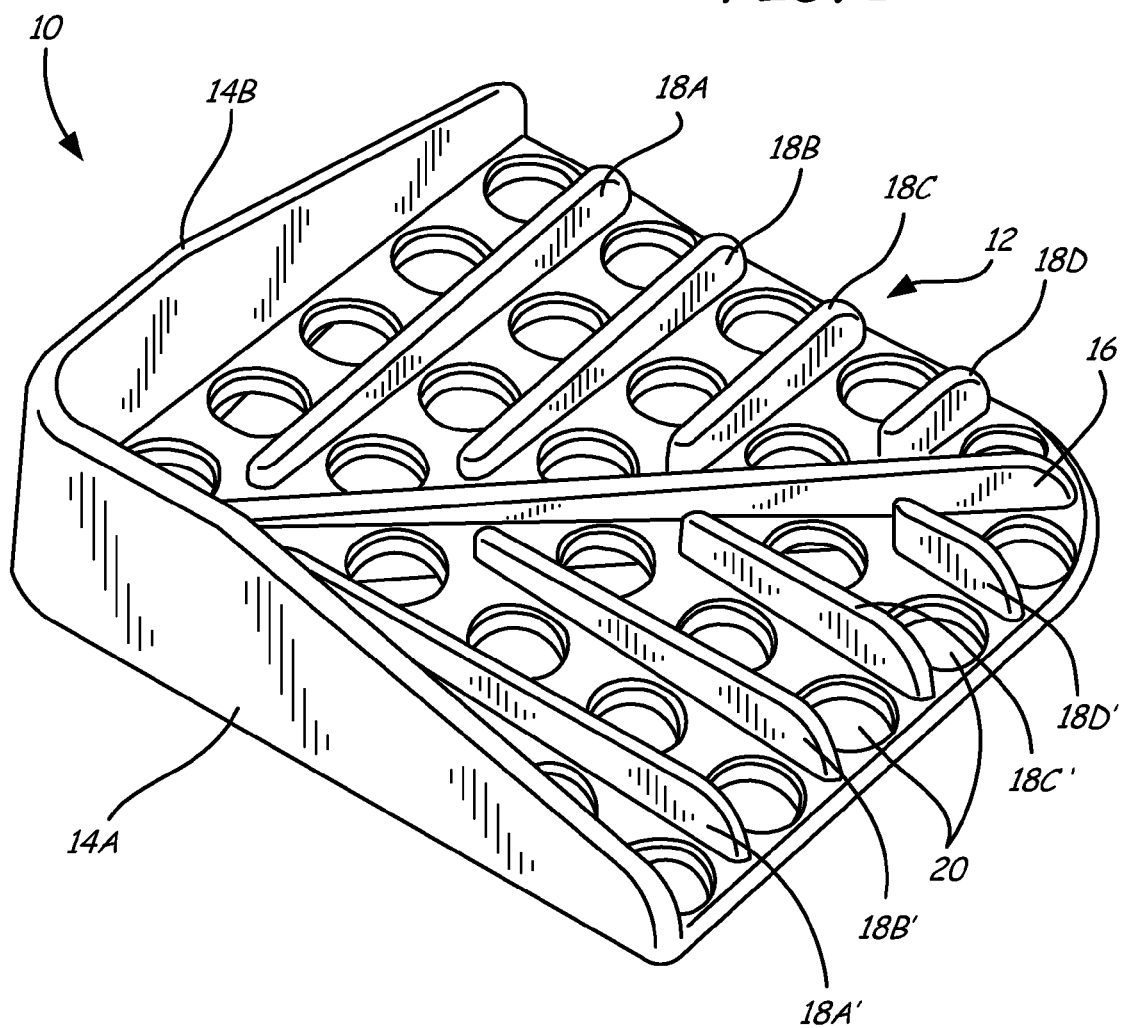
FIG. 1 is a top perspective view of a first embodiment of a surgical tray corner protector.

FIG. 1 is a top perspective view of surgical tray corner protector 10. Surgical tray corner protector 10 includes base 12, side walls 14A-14B, center support rib 16, side support ribs 18A-18D and 18A'-18D', and drainage apertures 20.

In the exemplary embodiment shown in FIG. 1, surgical tray corner protector 10 has a generally square shape. Side wall 14A extends from a first edge of base 12 and side wall 14B extends from a second edge of base 12. Side walls 14A-14B meet at a corner of surgical tray corner protector 10, and are used to position surgical tray corner protector 10 against a corner of a surgical instrument sterilization tray (not shown in FIG. 1).

Center support rib 16 extends from base 12 and runs diagonally from the junction of vertical side walls 14A-14B to the opposite corner of base 12. Side support ribs 18A-18D and 18A'-18D' also extend from base 12 and fan outward from center support rib 16. As shown in FIG. 1, four side support ribs 18A-18D are located on a first side of center support rib 16 and four side support ribs 18A'-18D' are located on a second side of center support rib 16. Center support rib 16 and side support ribs 18A-18D and 18A'-18D' form about a 45 degree angle with respect to each other. However, surgical tray corner protector 10 may comprise any number of central support ribs 16 and/or side support ribs 18A-18D and 18A'-18D', which may form varying angles with respect to each other.

In an exemplary embodiment, center support rib 16 and side support ribs 18A-18D and 18A'-18D' are each about 0.375 inches in width. The height of center support rib 16 gradually increases as center support rib 16 extends from the junction of vertical side walls 14A-14B. In addition, the height of side support ribs 18A-18D and 18A'-18D' also increases as side support ribs 18A-18D and 18A'-18D' extend from center support rib 16. In an exemplary embodiment, center support rib 16 has a length of about 4.244 inches and a height which increases from about 0.070 inches to about 0.269 inches. Side support ribs 18A and 18A' have a length of about 2.132 inches and a height which increases from about 0.208 inches to about 0.269 inches. Side support ribs 18B and 18B' have a length of about 1.607 inches and a height which increases from about 0.162 inches to about 0.269 inches. Side support ribs 18C and 18C' have a length of about 1.082 inches and a height which increases from about 0.116 inches to about 0.269 inches. Finally, in the exemplary embodiment shown in FIG. 1, side support ribs 18D and 18D' have a length of about 0.557 inches and a height which increases from about 0.070 inches to about 0.269 inches.

Center support rib 16 and side support ribs 18A-18D and 18A'-18D' define a support surface, which supports the weight of a surgical instrument sterilization tray and elevates the surgical tray from base 12. This prevents moisture from accumulating between the bottom surface of the surgical tray and base 12 during the sterilization process in the autoclave. In the exemplary embodiment shown, the heights of the ribs are tapered in a configuration that forms a support surface for a surgical tray in a horizontal plane, while base 12 tilts at an angle with respect to the horizontal plane. This allows moisture to drain along the angle of base 12. Also, in an exemplary embodiment, center support rib 16 and side support ribs 18A-18D and 18A'-18D' are not in contact with each other, which further reduces the concern of moisture retention and improves the air circulation during the drying process.

Although the support members of surgical tray corner protector 10 have been described and shown as ribs, it should be understood that other suitable supporting structures are also possible for supporting a surgical tray above the surface of base 12.

In the exemplary embodiment shown in FIG. 1, drainage apertures 20 are interposed between side support ribs 18A-18D and 18A'-18D' and extend through base 12. Drainage apertures 20 allow water to drain away from the surgical tray and improve air circulation, which aids in the drying process. In the exemplary embodiment shown in FIG. 1, corner protector 10 has thirty drainage apertures, which are positioned in rows between side support ribs 18A-18D and 18A'-18D'. However, the present invention may have any number of drainage apertures 20, which may form various configurations.

Surgical tray corner protector 10 is reusable and may be comprised, for example, of any suitable medical-grade polymeric material, such as silicone (40 Shore A Durometer Millable Silicone, in particular). This type of fluid-impermeable material further aids the ability of surgical tray corner protector 10 to resist the accumulation and retention of moisture, and allows surgical tray corner protector 10 to be reused multiple times without degradation of the material of the corner protector.

FIG. 2 is a bottom perspective view of surgical tray corner protector 10, which includes base 12, vertical side walls 14A-14B, drainage apertures 20, center support rib 22, and side support ribs 24A-24D and 24A'-24D'.

As described with respect to FIG. 1, vertical side wall 14A extends from a first edge of base 12 and vertical side wall 14B extends from a second edge of base 12. In an exemplary embodiment, center support rib 22 and side support ribs 24A-24D and 24A'-24D' on the bottom surface of base 12 are substantially aligned with respect to center support rib 16 and side support ribs 18A-18D and 18A'-18D' on the top surface of base 12 (shown in FIG. 1) and in effect form a mirror image of each other (although this correspondence is not necessary in all embodiments). Center support rib 22 and side support ribs 24A-24D and 24A'-24D' are also each about 0.375 inches wide and are not in contact with each other in an exemplary embodiment.

In contrast to center support rib 16, the height of center support rib 22 gradually decreases as center support rib 22 extends outward from the junction of vertical side walls 14A-14B. In addition, the height of side support ribs 18A-18D and 18A'-18D' also decreases as side support ribs 24A-24D and 24A'-24D' extend outward from center support rib 22. In the exemplary embodiment, center support rib 22 has a length of about 4.244 inches and a height which decreases from about 0.269 inches to about 0.070 inches. Side support ribs 24A and 24A' have a length of about 2.132 inches and a height which decreases from about 0.269 inches to about 0.208 inches. Side support ribs 24B and 24B' have a length of about 1.607 inches and a height which decreases from about 0.269 inches to about 0.162 inches. Side support ribs 24C and 24C' have a length of about 1.082 inches and a height which decreases from about 0.269 inches to about 0.116 inches. Finally, in the exemplary embodiment shown in FIG. 2, side support ribs 24D and 24D' have a length of about 0.557 inches and a height which decreases from about 0.269 inches to about 0.070 inches.

Center support rib 22 and side support ribs 24A-24D and 24A'-24D' define a support surface, which elevates corner protector 10 from a surface on which it is resting. This increases air flow and prevents moisture from accumulating between the bottom side of base 12 and the surface on which corner protector 10 is resting during the sterilization process in the autoclave. In an exemplary embodiment, the heights of the ribs are tapered in a configuration that forms the support surface in a horizontal plane, while base 12 tilts at an angle with respect to the horizontal plane. This allows moisture to drain along the angle of base 12. Also, in an exemplary embodiment, the plane of the bottom support surface (defined by center support rib 22 and side support ribs 24A-24D and 24A'-24D' shown in FIG. 2) is parallel to the plane of the top support surface (defined by center support rib 16 and side support ribs 18A-18D and 18A'-18D' shown in FIG. 1).

Figure 3A:
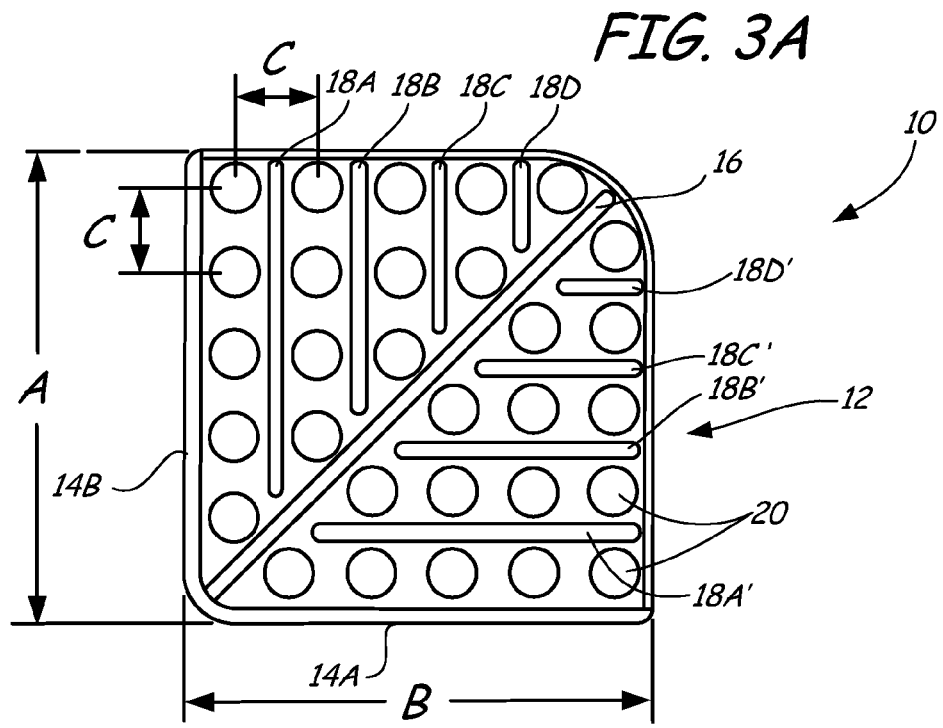
FIG. 3A is a top view of the surgical tray corner protector of FIGS. 1-2.

FIG. 3A is a top view of surgical tray corner protector 10, which illustrates exemplary dimensions of surgical tray corner protector 10. As described with respect to FIG. 1, in one exemplary embodiment, corner protector 10 has a generally square shape (although other shapes are contemplated in other embodiments, such as a generally rounded shape for an embodiment designed to be used with surgical trays having rounded corners). Corner protector 10 has a length of about 3 inches, as represented by line A, and a width of about 3 inches, as represented by line B. In addition, in the exemplary embodiment, as represented by line C, the distance between the radii of drainage apertures 20, which are adjacent to each other, is about 0.525 inches.

Figure 3B:
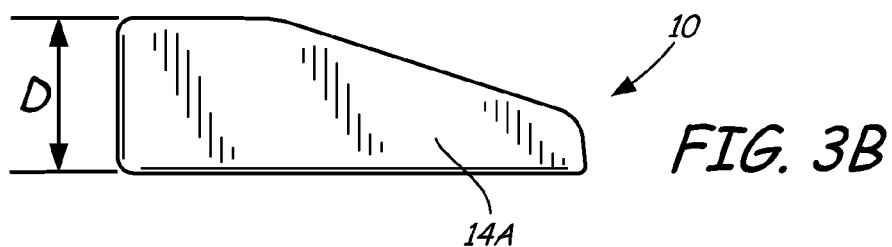
FIG. 3B is a side view of the surgical tray corner protector of FIGS. 1-2.

FIG. 3B is a side view of surgical tray corner protector 10, which illustrates exemplary dimensions of surgical tray corner protector 10. In the exemplary embodiment shown, vertical side wall 14A tapers from a height of 1 inch at its highest point, which is represented by line D, (and at which it adjoins to vertical side wall 14B, as shown in FIG. 1) to a height of 0.375 inches at its lowest point.

Figure 3C:
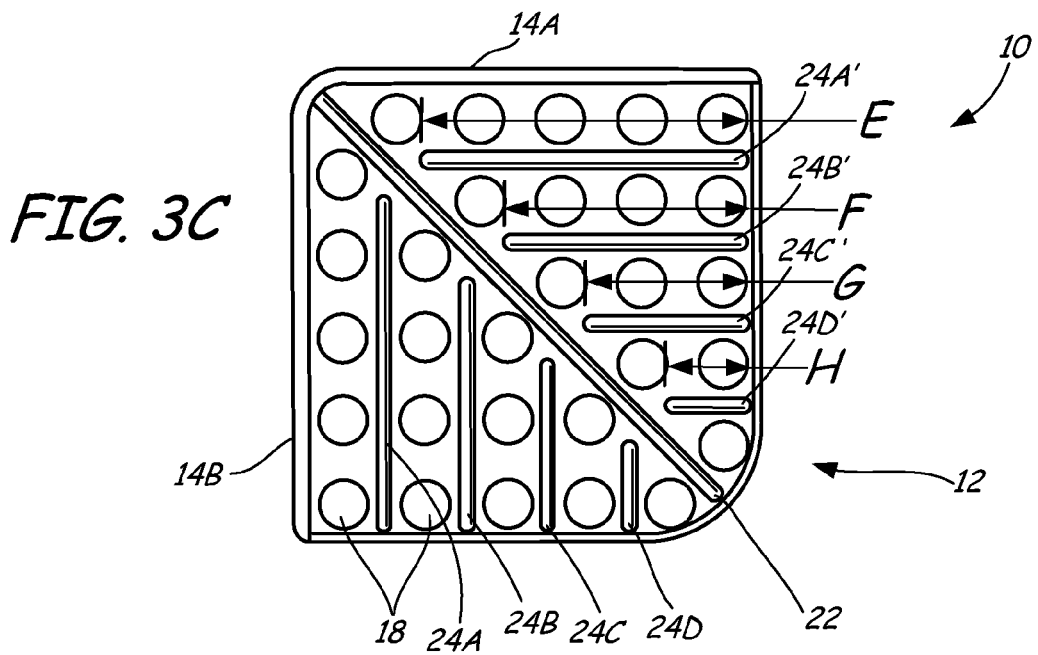
FIG. 3C is a bottom view of the surgical tray corner protector of FIGS. 1-2.

FIG. 3C is a bottom view of surgical tray corner protector 10, which illustrates exemplary dimensions of surgical tray corner protector 10. In the exemplary embodiment shown, thirty drainage apertures 20 are interposed between side support ribs 24A-24D and 24A'-24D'. As such, five rows of drainage apertures 20 are formed on either side of center support rib 22. As represented by line E, in a first row containing five drainage apertures 20, the distance from a first side of the first drainage aperture 20 to a first side of the fifth drainage aperture 20 is about 2.132 inches. As represented by line F, in a second row containing four drainage apertures 20, the distance from a first side of the first drainage aperture 20 to a first side of the fourth drainage aperture 20 is about 1.607 inches. As represented by line G, in a third row containing three drainage apertures 20, the distance from a first side of the first drainage aperture 20 to a first side of the third drainage aperture 20 is about 1.082 inches. As represented by line H, in a fourth row containing two drainage apertures 20, the distance from a first side of the first drainage aperture 20 to a first side of the second drainage aperture 20 is about 0.557 inches. The fifth row contains only one drainage aperture 20.

Figure 3D:
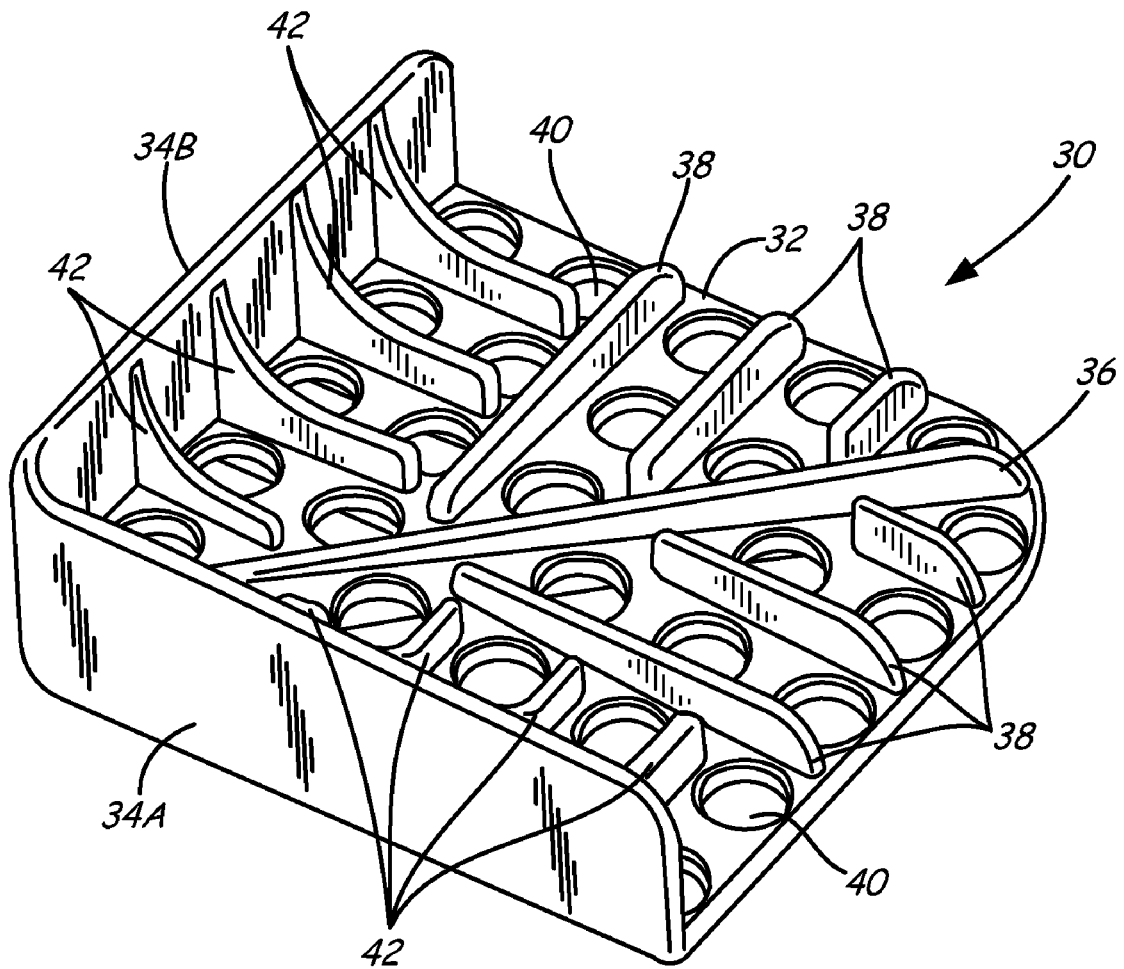
FIG. 3D is a top perspective view of an alternative embodiment of a surgical tray corner protector.

FIG. 3D is a top perspective view of surgical tray corner protector 30 according to an alternative embodiment. Corner protector 30 includes base 32, side walls 34A and 34B, center support rib 36, side support ribs 38, and apertures 40, similar to the features associated with corner protector 10 described above. The bottom of corner protector 30 may be formed with features that are similar to the top of corner protector 30 in an exemplary embodiment. Corner protector 30 also includes additional sloped support ribs 42 adjacent side walls 34A and 34B, with a portion of sloped support ribs 42 extending up at least part of side walls 34A and 34B. This embodiment is particularly appropriate for use with surgical trays that have rounded sides. The radii of sloped support ribs 42 can be adjusted to correspond to the curvature of the sides of a particular shape of surgical tray, so that corner protector 30 provides a snug fit against the sides of the surgical tray. Other configurations of ribs or other support members may also be designed in order to provide a desired fit with a surgical tray.

Figure 4:
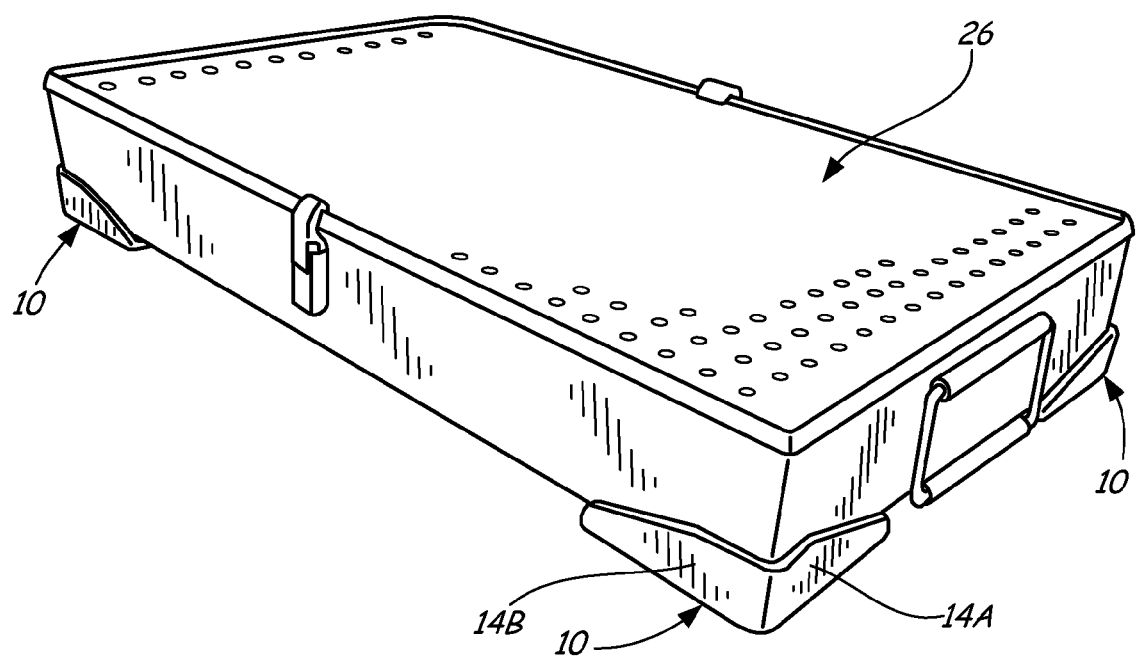
FIG. 4 is side perspective view of a surgical tray fitted with corner protectors.

FIG. 4 is side perspective view of surgical tray 26 fitted with corner protectors 10, which include side walls 14A-14B. Surgical tray 26 has square corners, and is therefore fitted with corner protectors 10, which also have a generally square shape. However, the present invention may also be configured for use with surgical trays which have circular or other shaped corners. Although surgical tray 26 is fitted with four corner protectors 10, only three corner protectors 10 are visible from this perspective.

Side walls 14A-14B assist in properly positioning surgical tray 26 on corner protectors 10. Side walls 14A-14B wrap around the horizontal walls at each corner of surgical tray 26. As surgical tray 26 rests on corner protectors 10, surgical tray 26 is elevated from the bases of corner protectors 10. This reduces the concern of moisture retention and improves air circulation during the drying process.

Corner protectors 10 create a protective barrier between the corners of surgical tray 26 and sterilization wrap, which is susceptible to tearing and ripping. As a result, after surgical tray 26 is wrapped and sterilized, corner protectors 10 will prevent the corners of surgical tray 24 from puncturing the plastic wrap during transportation and storage. The sterile environment in which the surgical instruments are stored is therefore maintained.

Although the present invention has been described with reference to preferred embodiments, workers skilled in the art will recognize that changes may be made in form and detail without departing from the spirit and scope of the invention.

The invention claimed is:

1. A method of providing a sterilized surgical tray, comprising:
    positioning a plurality of corner protectors at corners of the surgical tray, the plurality of corner protectors each having a support base with a plurality of apertures extending therethrough and a side wall extending along an edge of the support base on only two sides of the edge of the support base, the side wall having an inner surface and an outer surface, with the inner surface of the side wall and a top surface of the support base together forming a tray receiving interface;
    wrapping the surgical tray and the corner protectors with sterilization wrap, such that the corner protectors form a protective barrier between the corners of the surgical tray and the sterilization wrap;
    subjecting the wrapped surgical tray to sterilization; and
    drying the wrapped surgical tray after sterilization, wherein air circulates and/or fluid drains through the plurality of apertures extending through the support base of each of the corner protectors.

2. A method of providing a sterilized surgical tray, comprising:
    positioning a plurality of corner protectors at corners of the surgical tray, the plurality of corner protectors each having a support base with a plurality of apertures extending therethrough and a side wall extending along an edge of the support base on only two sides of the edge of the support base, the side wall having an inner surface and an outer surface, with the inner surface of the side wall and a top surface of the support base together forming a tray receiving interface;
    wrapping the surgical tray and the corner protectors with sterilization wrap, such that the corner protectors form a protective barrier between the corners of the surgical tray and the sterilization wrap;
    subjecting the wrapped surgical tray to sterilization; and
    reusing the plurality of corner protectors to provide another sterilized surgical tray.

3. The method of claim 1, wherein each of the plurality of corner protectors further comprises a plurality of standoff members on at least a portion of the tray receiving interface, and wherein positioning the plurality of corner protectors at the corners of the surgical tray further comprises spacing at least a portion of the tray receiving interface from the surgical tray with the standoff members.

4. A method of providing a sterilized surgical tray, comprising:
    positioning a plurality of corner protectors at corners of the surgical tray, the plurality of corner protectors each having a support base, a side wall extending along an edge of the support base on only two sides of the edge of the support base, the side wall having an inner surface and an outer surface, with the inner surface of the side wall and a top surface of the support base together forming a tray receiving interface, and a plurality of standoff members on at least a portion of the tray receiving interface, wherein positioning the corner protectors at the corners of the surgical tray comprises spacing at least a portion of the tray receiving interface from the surgical tray with the standoff members;
    wrapping the surgical tray and the corner protectors with sterilization wrap, such that the corner protectors form a protective barrier between the corners of the surgical tray and the sterilization wrap;
    subjecting the wrapped surgical tray to sterilization; and
    drying the wrapped surgical tray after sterilization, wherein air and/or fluid circulates through the space between at least a portion of the tray receiving interface and the surgical tray created by the plurality of standoff members.

5. A method of providing a sterilized surgical tray, comprising:
    positioning a plurality of corner protectors at corners of the surgical tray, the plurality of corner protectors each having a support base, a side wall extending along an edge of the support base on only two sides of the edge of the support base, the side wall having an inner surface and an outer surface, with the inner surface of the side wall and a top surface of the support base together forming a tray receiving interface, and a plurality of standoff members on at least a portion of the tray receiving interface, wherein positioning the corner protectors at the corners of the surgical tray comprises spacing at least a portion of the tray receiving interface from the surgical tray with the standoff members;

wrapping the surgical tray and the corner protectors with sterilization wrap, such that the corner protectors form a protective barrier between the corners of the surgical tray and the sterilization wrap;

subjecting the wrapped surgical tray to sterilization; and reusing the plurality of corner protectors to provide another sterilized surgical tray.

6. The method of claim 2, wherein each of the plurality of corner protectors further comprises a plurality of standoff members on at least a portion of the tray receiving interface, and wherein positioning the plurality of corner protectors at the corners of the surgical tray further comprises spacing at least a portion of the tray receiving interface from the surgical tray with the standoff members.

* * * * *

(12) EX PARTE REEXAMINATION CERTIFICATE (8868th)
United States Patent
Curnow et al.

(10) Number: US 7,780,136 C1
(45) Certificate Issued: Feb. 21, 2012

(54) SURGICAL TRAY CORNER PROTECTOR

(75) Inventors: Sam Curnow, Chanhassen, MN (US);
Ted Eric Ahrenholtz, Plymouth, MN (US)

(73) Assignee: General Hospital Supply Corporation, Monroe, NC (US)

Reexamination Request:
No. 90/011,654, Apr. 20, 2011

Reexamination Certificate for:
Patent No.: 7,780,136
Issued: Aug. 24, 2010
Appl. No.: 12/206,437
Filed: Sep. 8, 2008

Related U.S. Application Data

(63) Continuation of application No. 11/950,246, filed on Dec. 4, 2007, now Pat. No. 7,422,185, which is a continuation of application No. 11/779,089, filed on Jul. 17, 2007, now Pat. No. 7,413,157, which is a continuation of application No. PCT/US2006/030297, filed on Aug. 2, 2006.
(60) Provisional application No. 60/705,245, filed on Aug. 3, 2005.

(51) Int. Cl.
*A47B 95/00* (2006.01)

(52) U.S. Cl. .................. 248/345.1; 248/346.5; 206/453; 206/586

(58) Field of Classification Search ................ 248/345.1
See application file for complete search history.

(56) References Cited

To view the complete listing of prior art documents cited during the proceeding for Reexamination Control Number 90/011,654, please refer to the USPTO's public Patent Application Information Retrieval (PAIR) system under the Display References tab.

*Primary Examiner* — Jeanne M Clark

(57) ABSTRACT

A surgical tray corner protector includes a support base, a side wall extending along an edge of the support base, and a plurality of apertures extending through the support base to form a tray support surface, providing improved drainage and air flow.

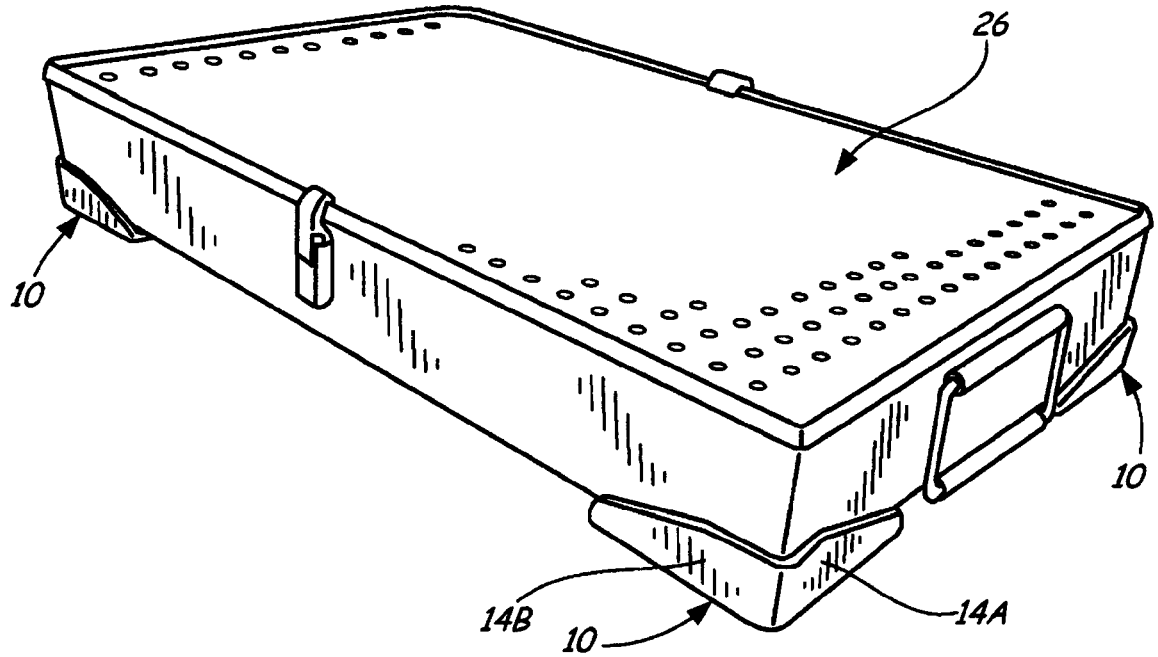

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-6 are cancelled.

* * * * *